(12) United States Patent
Sun

(10) Patent No.: US 10,974,005 B1
(45) Date of Patent: Apr. 13, 2021

(54) TIP ADJUSTABLE STYLET

(71) Applicant: Yang Sun, San Francisco, CA (US)

(72) Inventor: Yang Sun, San Francisco, CA (US)

( * ) Notice: Subject to any disclaimer, the term of this patent is extended or adjusted under 35 U.S.C. 154(b) by 601 days.

(21) Appl. No.: 15/851,667

(22) Filed: Dec. 21, 2017

(51) Int. Cl.
*A61M 16/04* (2006.01)
*A61M 25/09* (2006.01)

(52) U.S. Cl.
CPC .... *A61M 16/0488* (2013.01); *A61M 16/0418* (2014.02); *A61M 2025/0915* (2013.01)

(58) Field of Classification Search
CPC .......... A61M 16/0488; A61M 16/0418; A61M 2025/0915; A61M 25/09025; A61M 25/0147; A61B 1/267
See application file for complete search history.

(56) References Cited

U.S. PATENT DOCUMENTS

| | | | | |
|---|---|---|---|---|
| 6,413,234 B1* | 7/2002 | Thompson | ........ | A61M 25/0136 600/434 |
| 6,718,970 B2* | 4/2004 | Sniadach | .......... | A61M 16/0418 128/200.26 |
| 8,695,590 B2* | 4/2014 | Parker | ............ | A61B 17/320016 128/200.26 |
| 9,199,051 B2* | 12/2015 | Booth | ............... | A61M 16/0488 |
| 10,149,957 B2* | 12/2018 | Runnels | ............ | A61M 16/0488 |
| 2012/0073572 A1* | 3/2012 | Li | ...................... | A61M 16/0418 128/200.26 |
| 2018/0250484 A1* | 9/2018 | McCormick | ............. | A61B 1/05 |

* cited by examiner

Primary Examiner — Margaret M Luarca

(57) ABSTRACT

Present invention is a tip adjustable stylet to be inserted into a tubular structure and to be pushed out its distal aperture to form curvatures. The device comprises a bendable member, a retracting string, an intersegment and a control handle. The bendable member has a control ring at its proximal end and a tip at its distal end. An operator can push the bendable member distally from the proximal end along the lumen of the tubular structure. Predetermined extensibility and length of the retracing string limit distance of the bendable member being pushed and hold the distal portion of the bendable member backward when the bendable member is been pushed forward outside of the tubular structure's distal aperture, thereby to bend the distal portion of the bendable member into the curves therefore to move its tip to a target location, such as patient's vocal cords opening.

22 Claims, 9 Drawing Sheets

Fig6
Fig6a
Fig6b
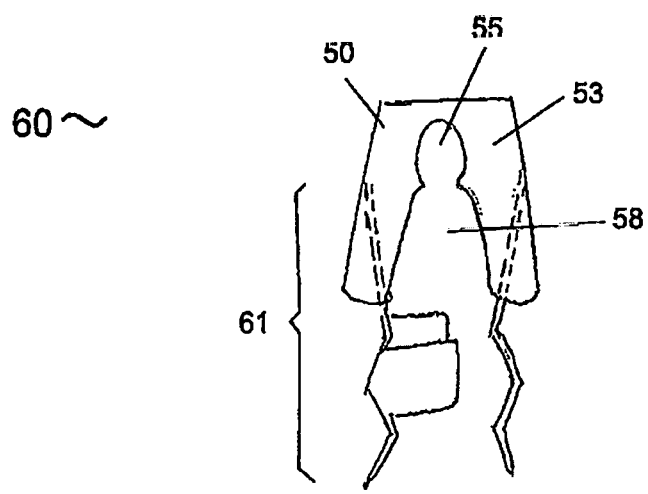
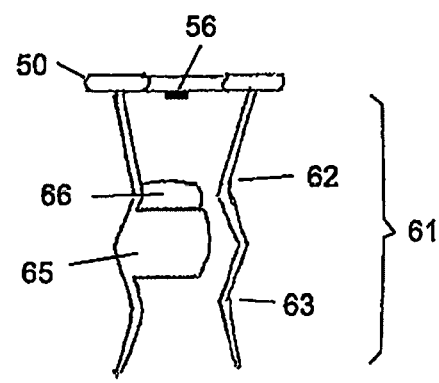

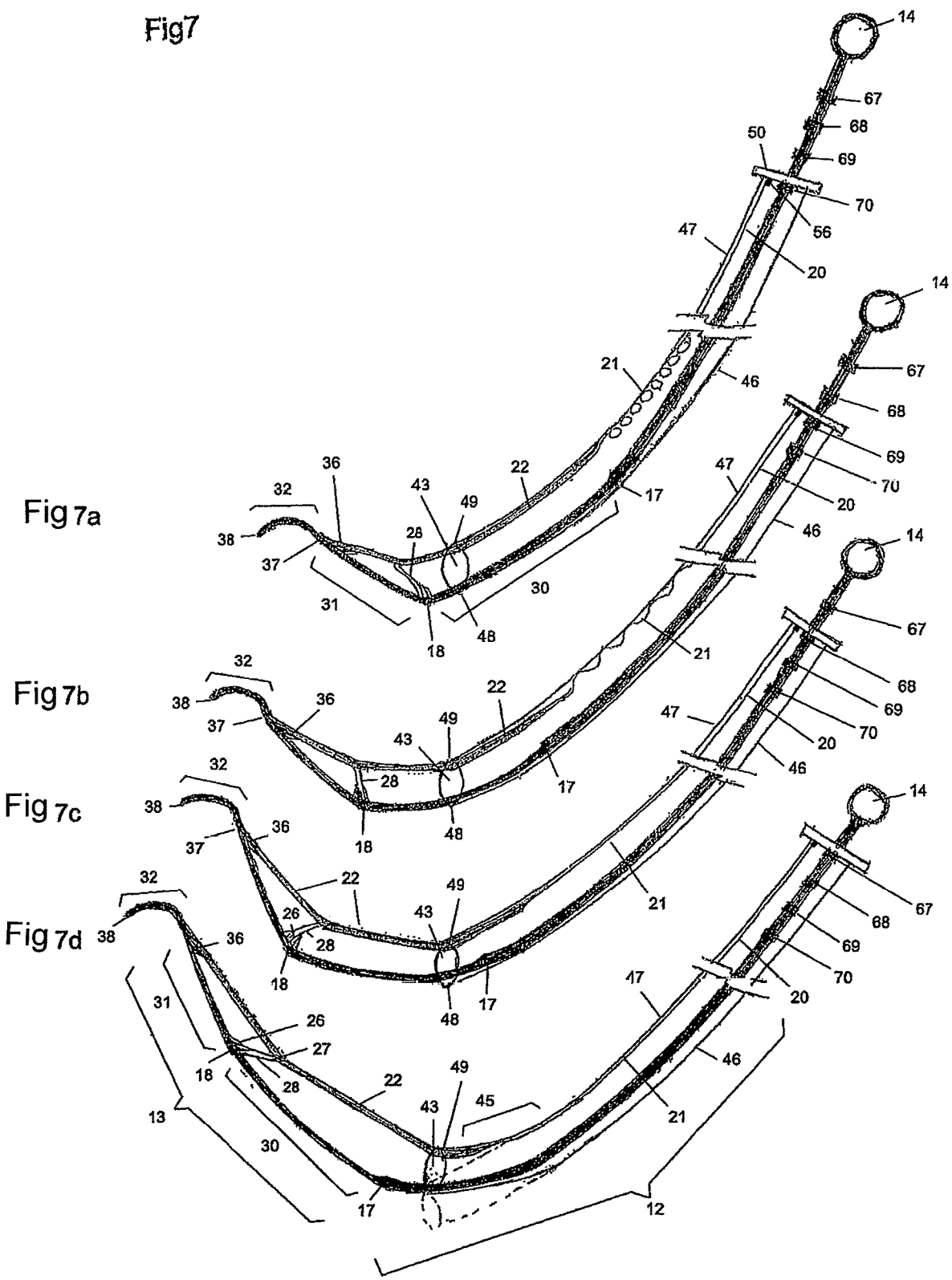

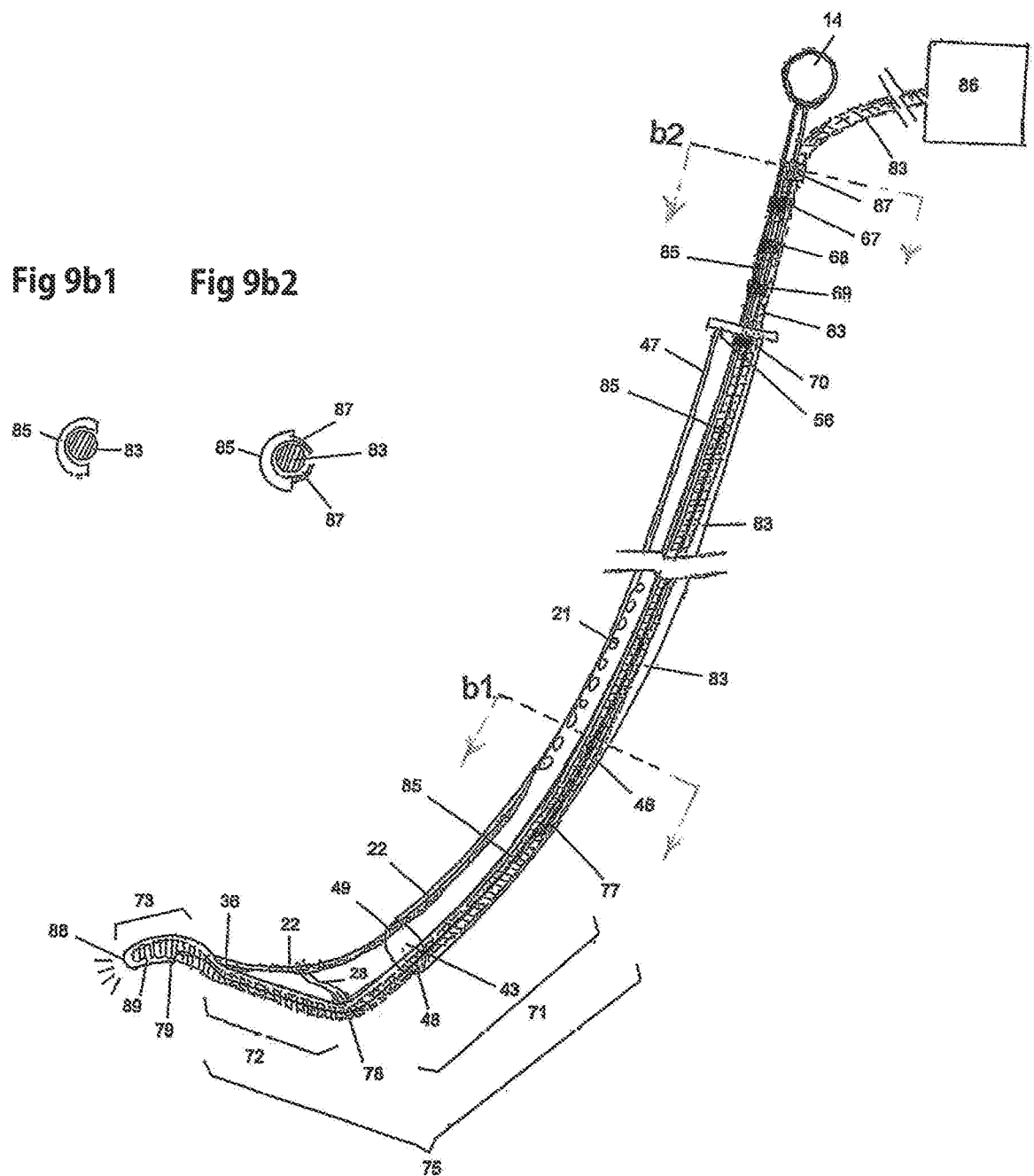

TIP ADJUSTABLE STYLET

BACKGROUND

Endotracheal tubes, brief as ET, have been utilized in a wide variety of medical specialties in past decades for airway management. Many intubation tools have been developed to effectively insert an endotracheal tube into a patient's trachea. An intubation process can often be difficulty because of the contours and obstacles encountered in a patient's airway. A patient's airway anatomy varies from patient to patient. As the endotracheal tubes are generally made to a standard curvature, it is often necessary to impart a greater bend to the tip of the tube in order to be inserted into a trachea. Many prior art devices have been developed to try to resolve these problems. One of the examples is a metal malleable stylet which can be inserted into an endotracheal tube and be bent at a desirable curvature by an operator before starting intubation process, but the operator will not be able to change the curvature of the stylet as needed during the intubation unless the endotracheal tube is pulled out, the curvature changed, and then again inserted. The interruption of intubation and delay in intubation often are undesirable when the need to ventilate the patient is urgent.

The currently commercially available video laryngoscopes can provide good visualization if use properly. However, good visualization is not equal to good intubation. The limitations of the rigid stylet in advancing the ET through to the vocal cords and into the trachea have been well documented. In the recent decade, more and more commercially available Video laryngoscopes have created the need for more dynamically adjustable stylets to accommodate the unique angles and turns of a glottic opening area under vision of the video laryngoscope. An example of a commercially available articulating stylet is by Parker Medical Inc., U.S. Pat. No. 8,695,590 B2, a stylet inserts into an ET and its tip can be manually adjusted when the ET approaches the glottis opening. Like all other types of stylets in which the distal tip of the stylet is stayed inside of an ET and positioned at distal opening of the ET. The stylet will make tip of the ET more rigid and often times make the curved tip of the ET very hard to align with a patient's glottic opening. As result, the ET's distal opening bevel often becomes stuck at the arytenoids, or anterior edge of the glottic opening. Even though an operator can have a good view of the vocal cords by video laryngoscope, the stylet is difficulty to align with glottic opening and difficult to guide the ET through the vocal cords opening. Thus, there is an increased chance of trauma to vocal cords and surrounding tissues. Such as recently commercially available "Truflex" stylet uses metal stylet to adjust the curvature of the distal tip of an endotracheal tube which can be quite traumatic to the airway anatomy. Other prior arts, U.S. Pat. No. 8,505,590, 2015/0182717, in all these prior arts, the tips of the stylet are inside the distal opening of the endotracheal tube during the process of bending the endotracheal tube which make the bendable tip of the stylet hard manipulate and make the ET distal end become a rigid curve. The rigid curve of the ET distal end makes the stylet distal tip very hard to guide the ET into the laryngeal opening even though distal end of the ET has already in front of the glottic opening.

SUMMARY OF INVENTION

The present invention is an articulating stylet. The first aspect of the present invention is directed toward an intubation stylet for intubating a trachea. For the purpose of an endotracheal intubation, a traditional laryngoscope or a video laryngoscope is needed for visualization. However in many clinical scenarios, often time a medical practitioner needs to reach or examine a patient's and animal's narrow body space or detoured passages which could not be normally reached by a human hand or a straight shaped equipment. Those examination or treatment procedures may need an articulating stylet with a bending capability to reach these destinations. And the concept and basic design principle of the present invention is capable to be used to design similar equipment to be used in different medical fields even in an animal medical care. When used in those clinical scenarios, a tubular structure can be used to replace an endotracheal tube and is also able to be bent on its distal portion of the device by an operator under varies kind of visualizations directly or indirectly. In following descriptions, the term of ET and tubular structure are interchangeably used.

The articulating stylet comprises a control handle, two elongated flexible members which are a bendable rod and a retracting string, and an intersegment. The device is to be inserted into and passed through an ET with distal portion of the device positioned outside of the ET distal aperture before the device can perform its function. Flexibility and resilient of the distal portion of the device and control from proximal end of the device enable an operator to manipulate a distally located bendable segment to form curvatures and thereby position or change a position of the distal tip of the device while the majority of the device is positioned inside the ET. In comparison with above mentioned prior arts, the distal portion of the present stylet is positioned outside of an ET's distal aperture and can be manipulated by an operator from proximal end of the stylet to bend or form curves. This future has given the present invention a capability to overcome above mentioned insufficiencies in the prior art devices.

The control handle functions as a coupling mechanism for holding the bendable rod and retracting string, and the ET together. The control handle comprises a docking plate and two holding plates. The docking plate provides an attachment point for the retracting string, a sliding hole for the bendable rod sliding distally or proximally and a docking hole to dock the bendable rod at a specific position. The two holding plates will hold the ET in between and provide a place for an operator to hold the assembly too. The ET will serve as a restraint means to keep the two elongated members in proximity. And the upper edge of the ET's distal aperture provides anchor points or a sliding point for the retracting string sliding back and forth.

The bendable rod, from proximal to distal end, comprises a proximal segment, a middle segment, a bendable segment, and a tip segment. The distal tip of the rod or the device is the most distal end of the tip segment. The bendable rod is configured to have control ring at its proximal end for an operator to move the bendable rod distally or proximally. The bendable segment is further divided into a first bending section and a and second bending section. The both bending section form a bending section joint between them. From the bending section joint to the distal tip of the rod is distal portion of the bendable member, the rod. And the bendable segment also forms a bendable junction with the middle segment. These two bendable points can be bent when an external force applied and will play major role in bending and curvature formation. They will be bent at different stages during the bending process. However alternatively the bendable segment can be configured in only one segment therefore there is not bending section joint, or can be configured in more than two bending sections and therefore can have more than one bending section joint.

The retracting sting can be a filament-like or thin belt-like elongated flexible material. From a distal to proximal direction, the retracting string can be subjectively divided and described as a distal segment, a coiled filament and a proximal filament. The proximal end of the retracting string is configured to firmly attach to the control handle. The distal end of the retracting string is coupled to the distal portion of the bendable rod. The coiled filament which is an only portion of the retracting string can be stretched and elongated in a predetermined distance. The coiled filament has an elastic property and will be able to generate pulling force when being stretched and elongated. And alternatively, whole length of the retracting string can be configured to be extensible. The extensibility of the retracting string allows the bendable rod to be able to be pushed out of the ET distal aperture.

An intersegment has been configured and positioned between the two elongated member's distal portion to hold the two elongated member in proximity and participate in bending the bendable segment during third staged push. Alternatively more than one intersegment can be configured can be configured.

The first and second bending section of the bendable segment and the two bendable points are configured to be bent when a retraction force is applied. Retracting string's distal end is preferably coupled to the distal end of the bendable segment where the bendable segment is in conjunction with the tip segment or alternatively can be coupled to the distal portion of the bendable member. The retracting string also coupled to the bending section joint of the bendable segment through an intersegment. The retracting string can generate a pulling force when the coiled filament is stretched and provides a holding force when the coiled filament has been stretched taut, as result of an operator is pushing the control ring to advance the rod distally inside the lumen of the ET. Therefore the bendable segment can be bent to different angles and curves, and thereby distal tip of the bendable rod can navigate the obstacles of a patient's airway and be moved toward to the vocal cords opening.

This process can be subjectively divided into three stages to describe the changing process of the curves. In present invention, the four transverse protrusions along the proximal segment of the bendable rod and three staged push have been configured to generate different predicable different curvature configurations. However an operator can choose to consciously pushing the rod without stopping at each stage until the tip of the rod reach a desired position.

The rod is a guiding member with its distal tip moving toward and into vocal cords opening and trachea by an operator pushing a control ring at the rod proximal side. The crescent shaped of the tip segment of the bendable member of the stylet is easier aligned with the vocal cords opening and has smooth surface. The position of the tip segment is controlled by the tension on the retracting string, location and bendability of the two bendable points, flexibility and length of the first and second bending sections of the bendable segment, and position of the bendable segment inside the ET lumen. An operator is able to move the distal tip in front of and through the vocal cords by pushing or pulling the control ring at proximal end of the bendable member. Once the tip is through the vocal cords, the ET can be slid along the stylet and into the trachea.

The materials forming the bendable rod, retraction string and control handle are preferably plastics, or polymers or metal or combination of all with properties of flexible, resilient and elastic. In general, the control handle is made with material that is more rigid than the rod, and the rod is made with materials that are more rigid than the retracting string.

BRIEF DESCRIPTION OF THE DRAWINGS

FIG. 6a—A top view of the control handle, the docking plate slightly slanted towards reader, please note that in all embodiments of the present invention the control handle has the same configuration.

FIG. 6b—Side view of the control handle of FIG. 6a.

FIG. 7—Schematic drawing in comparison of the curvature of the distal portion of the rod at positions of by first, second, and third push and being locked at a position by a corresponding transverse protrusion. In order to demonstrate transverse protrusions and their docking positions, holding plates is not shown.

FIG. 7a—Left side view, the device inserted into the tubular structure and configured in a set-up configuration. The distal portion of the rod, the retracting string and intersegment are positioned outside of an ET distal aperture or a tubular structure. First transverse protrusion is docked under the docking plate.

FIG. 7b—Left side view, a curvature formation after the rod is pushed to a first docking position.

FIG. 7c—Left side view of the curvature after the rod pushed to a second docking position.

FIG. 7d—Left side view of the curvature after the rod pushed to a third docking position. Please note that the ET distal segment 45 is lifted up slightly by the tautened distal retracting segment of the retracting string. Dotted lines indicate position of the tubular structure distal retracting segment before being lifted.

Please note, in all FIG. 7a, 7b, 7c, 7d, the tubular structure is imaginarily held in the same position when the first, second and third push are executed. The intersegment is gradually moved from a more horizontal position at the set-up configuration to reverse its orientation where it becomes part of the retracting means to hold back the bendable segment of the rod and thereby making the bendable junction bend.

Figure 8:
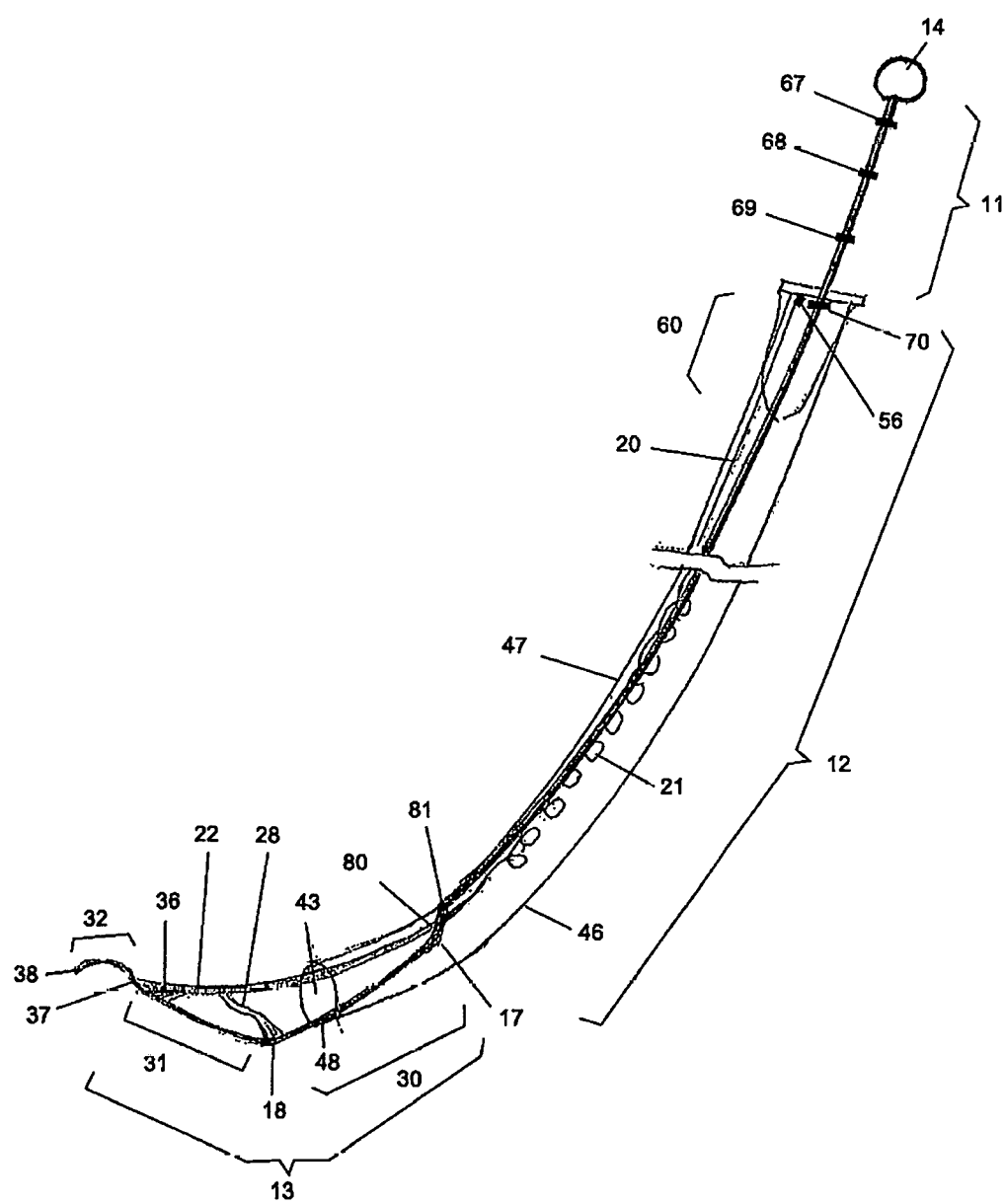

FIG. 8—A second embodiment of the present invention.

FIG. 9—A third embodiment of the present invention.

Figure 1:
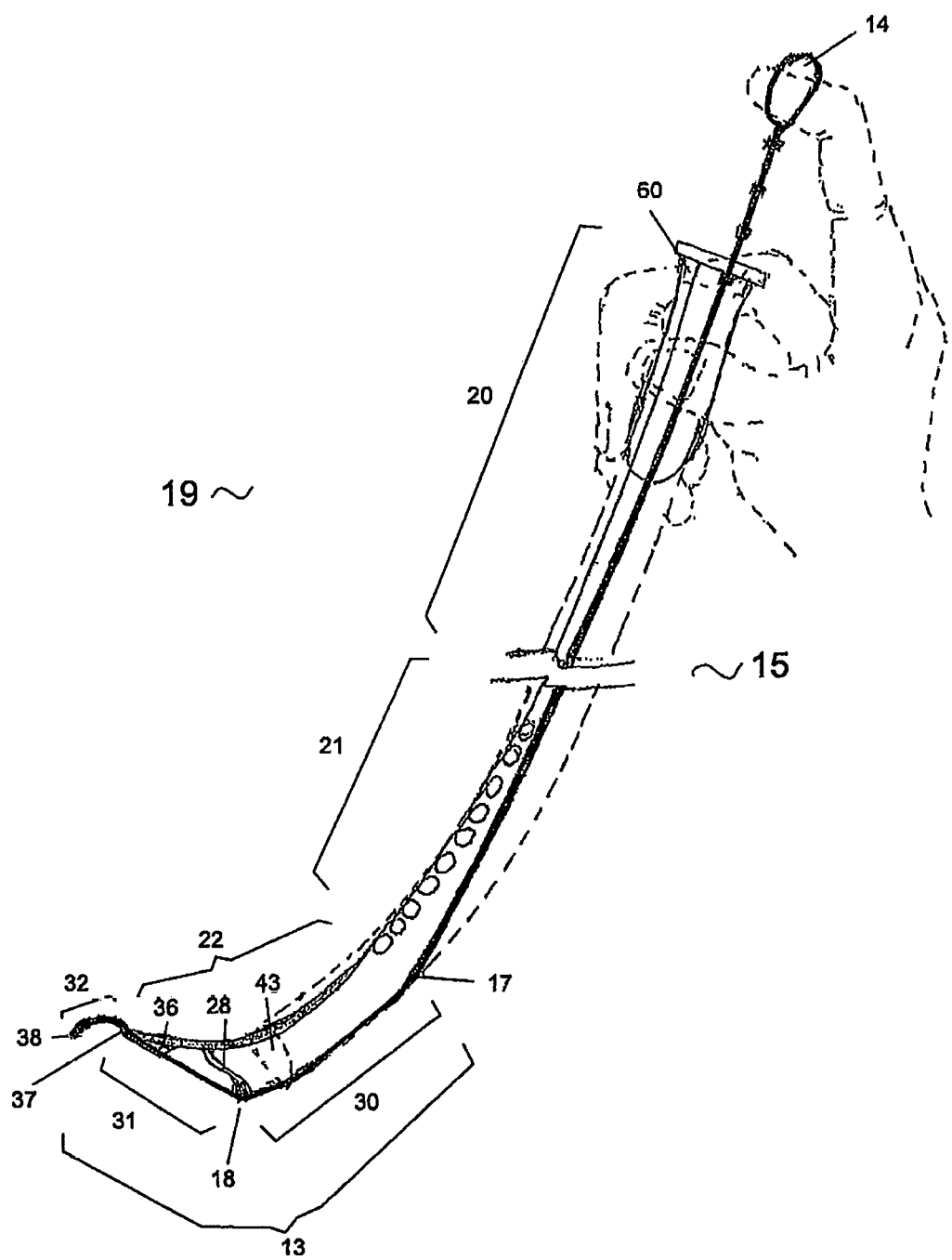
FIG. 1—shows a side view of the device in a set-up configuration, which means the device has been inserted into a tubular structure and the tubular structure has been secured and is not able to move up and down over the device during the operation, and the ET and device together are ready to be inserted into patient's mouth.

FIG. 9b1—A cross-sectional view of the device with a fiber-optic scope probe pressed into the bendable shell taken along the line b1-b1 of FIG. 9 in accordance with the third embodiment of the present invention.

Figure 2:
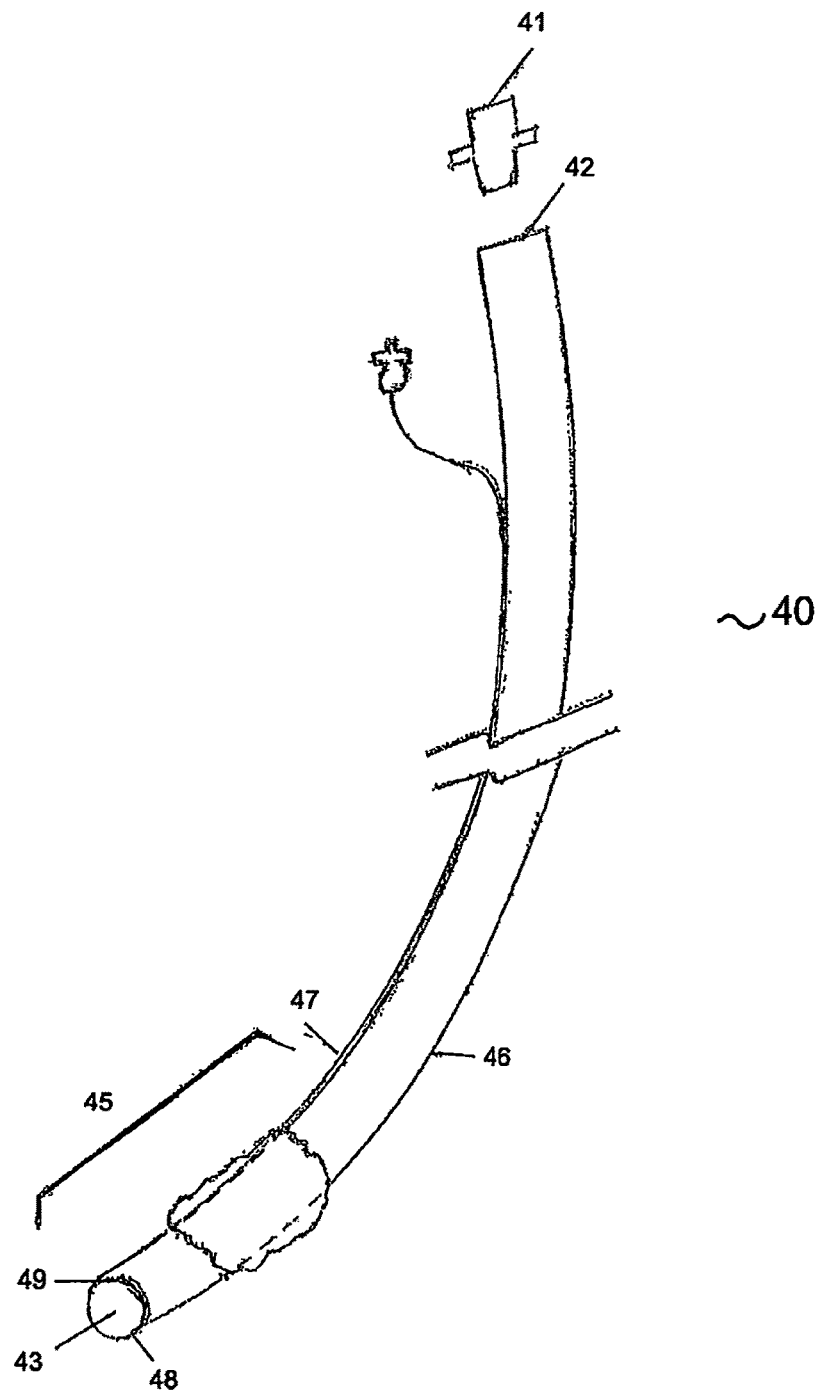
FIG. 2—A side view of an endotracheal tube, brief as ET.

FIG. 9b2—A cross-sectional view of the device with a fiber-optic scope probe pressed into the bendable shell taken along the line b2-b2 of FIG. 9 in accordance with the third embodiment of the present invention.

DETAILED DESCRIPTION OF THE PREFERRED EMBODIMENT OF THE PRESENT INVENTION

Even though the device can used in variety of applications such as GI tube placement, or any need for visualization of a physically small space with limited access area where visualization is only possible through the a narrow passage, the following description will use the an ET during an airway management as an example to illustrate the device's parts and basic design concept.

The total of three embodiments based on the same novel concept and design are described. Though, more alternative designs can be derived from the disclosed preferred embodiments. They are all within the scope of the protection of the present invention.

As used in this application, the word "member" refers to a structural element. For purpose of the drawing and description, the use the word of "proximal" refers to an end of the stylet closest to the operator when an operator holds the device and is ready to insert the device into a patient's mouth. The reference to the term "distal" refers to an end that first enters into a patient's mouth and is opposite end of the proximal end. Therefore, the distal tip of the device is always points distally. Therefore, when an operator pushes bendable member distally, also described as push "forward or down". The term ET represents an endotracheal tube or a tubular structure in general. The word "posterior" refers toward a back side of an operator or patient's body or patient's back pharyngeal wall. The word "anterior" refers to the front side of an operator or patient body or toward the glottic opening. A commonly used ET is longitudinal hollow tube with proximal aperture and distal aperture. The proximal aperture has an adaptor for connecting with a respiratory machine. The adaptor will be removed before assembling the device with an ET. In medical practice, an ET has always been held in an orientation where the ET bevel is facing to an operator's left. Therefore, for purpose of easy description and understanding, in following description and drawings an ET orientation is facing towards the reader. All drawings are views from left side. Therefore, the ET distal aperture is always facing towards the reader. A concave side of an ET will be described as "anterior aspect or anterior wall" because the ET's anterior wall is always inserted toward front side of patient's body. Vice versa, a convex side of the ET will be described as the "posterior aspect or posterior wall". For easy understanding, in all drawings "front" or "anterior" is on left side and "back" or "posterior" right on right side. Since this device can be used in a patient and an animal, the term of "patient" represents human patient and animals.

First Embodiment

Referring to FIG. 1, shown is exemplary of the present invention in set-up configuration or set-up position after the stylet device inserted into an ET. FIG. 1 shows a left side view of the device being assembled in set-up position, which means the device has been inserted in to an ET 40 and the ET 40 has been held and not able to move up and down over the device, and not able to move forward and backward during the operation. The ET 40 and device together are ready to be inserted into patient's throat. From FIG. 1 to FIG. 8, the bendable member is a rod 15.

To prepare to use the device, an operator will lubricate bendable segment 13, middle segment 12 of the rod 15, and the distal retracting segment 22 of the retracting string 19. A length of the distal portion of the retracting string 19 and the rod 15 are inserted into an ET 40 with the edge of the ET distal aperture 43 matching a loading reference point 39. The loading reference point 39 is a symbol or mark on the bendable segment 13. The loading reference point 39 is located at about one fifth or one third from the distal end of whole length of the first bending section 30. At present invention, the loading reference point 39 is recommended to match the edge of the ET distal aperture 43 during assembly of the device with an ET 40. This will consistently leave a length of the bendable segment 13 of the rod 15 outside of the ET distal aperture 43. In addition four quantitatively spaced transverse protrusions 67-70 along the proximal segment 11 of the rod can give an operator an opportunity to perform three consistently distanced pushes and therefor most likely produce three predictable curvature formation along the bendable segments 13 and predictable distal tip position 38, even though there can be some variations due to different size of the ET with different flexibility or made by different manufactures. However, an operator can load an ET over the device little more proximally or distally according a specific patient's airway anatomy. It is recommended that after assembling the device with the ET before inserting the device and ET into a patient's throat, an operator can try to push the rod distally either quantitative or continuously to get estimate of bending angles and curvature formation and the rod tip 38 position to estimate where to load the ET related to the loading reference point 39 to fit a specific patient's anatomy. Even though the stylet can be manufactured in three or more different sizes and lengths to be used in different sizes and lengths of ET 40, but there are more than eight different sizes and lengths of the ETs therefore for each specific size and length of the stylet, by matching the loading reference point 39 with the ET distal aperture, the ET proximal aperture 42 may or may not reach the lower surface of the docking plate 50 at set-up position and during operation. However the control handle 60 is still able to hold the ET proximal portion and prevents the ET's unnecessary movement.

Two ET holding plates 61 will hold a length of the proximal portion of the ET 40. The set-up transverse protrusion 70 will be placed under the docking hole 55 and the rod will stay inside of the docking hole 55 until an operator moves the rod 15 outside of the docking hole 55. This called the set-up position. When the rod 15 is in its set-up position, the retracting string 19 will be pulled in tension slightly but the coiled filament 21 remains un-extended coiled state. Before inserting into a patient's mouth, the operator's one finger of a dominated hand, preferably index finger, will be placed into the control ring 14 and other fingers will grip two ET holding plates 61 as shown in the FIG. 1.

Figure 3:
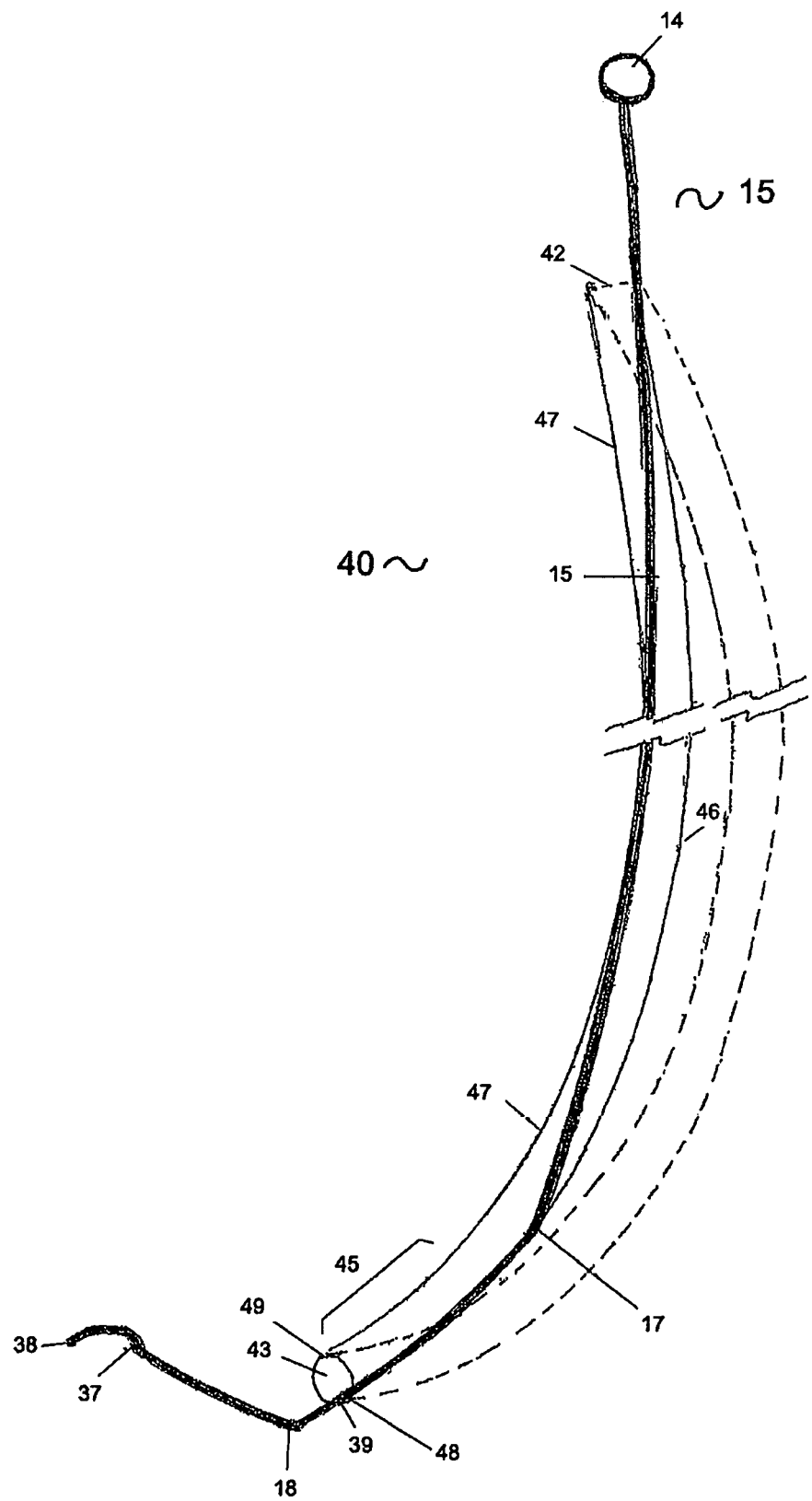
FIG. 3—Left side view of the rod being inserted into a tubular structure or an ET, to demonstrate flexibility and elasticity of the tubular structure curvature and the rod, and their interacting when the rod is in the set-up state. Dotted line shows the curvature and shape of the tubular structure before the rod is inserted into the tubular structure. If a tubular structure is an endotracheal tube, the rod is constructed more rigid than the ET. In order to clearly and completely demonstrate features of the rod the control handle and restricting string are not shown.

FIG. 2 is a left side view showing a commonly used ET 40, and FIG. 3 showing interaction between the ET's preformed curvature and the rod's flexibility and rigidity. An ET 40 has proximal aperture 42 after removing a 15 mm standard the connector 41. The ET 40 has a left-faced beveled distal aperture 43. The length of 3-6 cm from the ET distal aperture 43 to the proximal direction is called the ET distal segment 45. The left-faced beveled distal aperture 43 is circular shaped and has an upper edge 49 on top of the circle and lower edge 48 on bottom of the circle. The ET 40 has a preformed bow like curvature which is changeable. The proximal 11 and middle segment 12 of the rod 15 are slightly bent and made of materiel with more rigidity and can make the ET 40 more straight from its original bow shape. The rigidity of the proximal 11 and middle segment 12 of the rod 15 will decrease the curvature of the ET 40. However, the curvature of the ET can bend the rod a small extent, especially at the junction of the middle segment 12 and bendable segment 13, called bendable junction 17. Due to the ET 40, the bendable segment 13 is much more curved than the proximal and middle segment of the rod 15, the bendable junction 17 most likely touches the ET posterior inner wall. Therefor after the set-up position, the bendable segment 13, at least partially, is always touching the ET posterior inner wall after the device is inserted into the ET and remains in that relationship during operation until the bendable segment 13 is pushed out of the ET distal aperture 43. After the device is inserted in an ET 40, the ET will hold the two elongated members, the rod 15 and retracting string 19 inside its lumen to prevent the separation from each other during use of the device. The ET distal aperture 43 also can hold the rod 15 and retracting string 19 in proximity to limit their deviation from each other during operation.

Figure 4:
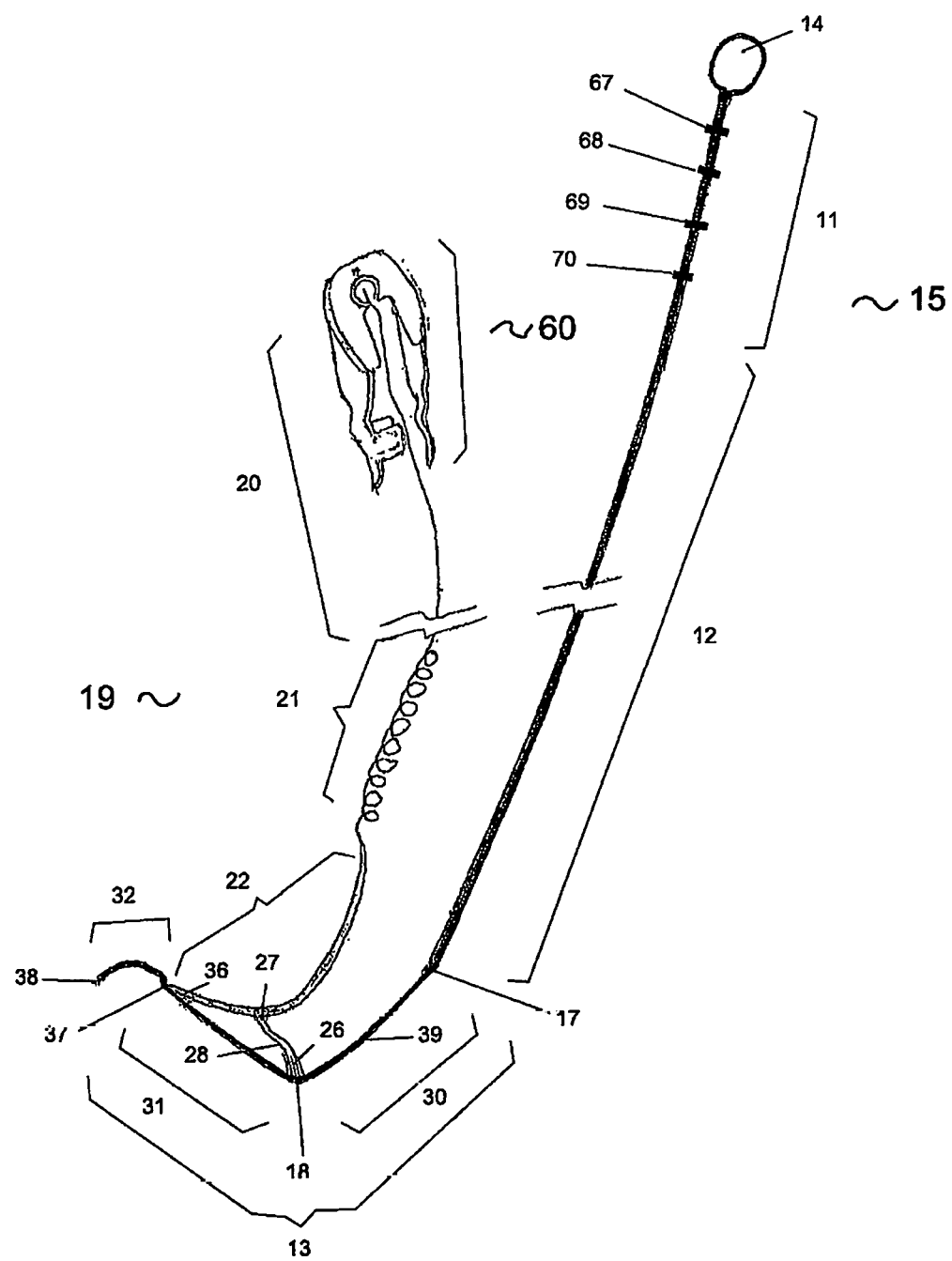
FIG. 4—A left side view of the first embodiment of the present invention before insertion into a tubular structure, the retracting string is in a loose state, and control handle not in contact with the rod. The rod bendable segment is in its preformed curved shape.
Figure 5:
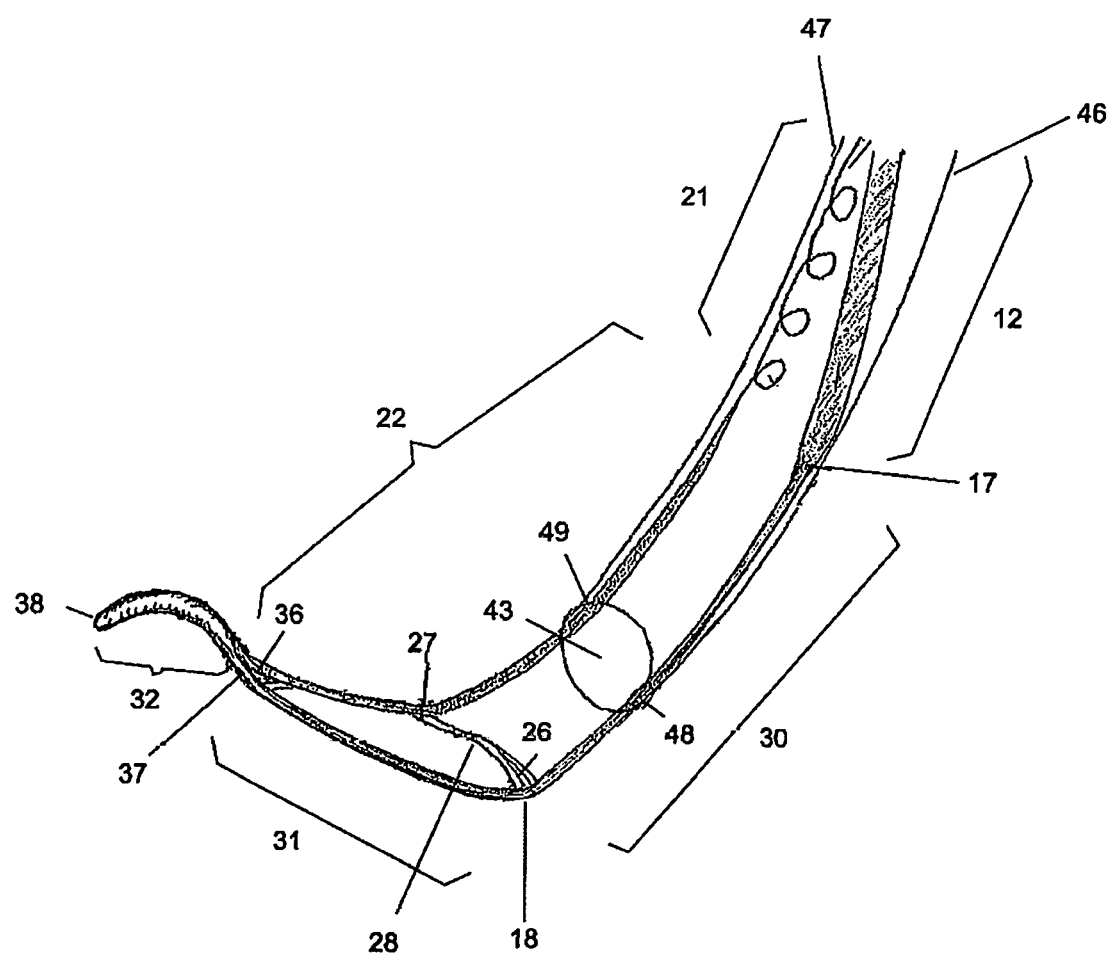
FIG. 5—Closed-up view of distal portion of the device of the FIG. 4 after being inserted into an ET in set-up position.

Referring to FIG. 4, the device comprises four components, a control handle 60, a bendable member called rod 15, a retracting string 19 and an intersegment 28. Referring to FIG. 5, a zoomed up more detail view of the distal portion of the device after being inserted into an ET in set-up position is shown.

The control handle 60 does not physically attach to the rod 15 until device assembly with an ET 40 at set-up. After the device is inserted into an ET 40 and configured in the set-up position, the rod 15 is normally received through sliding hole 58 on the docking plate 55 such that distally sliding of the rod 15 can increases the bending in the bendable segment 13 and move forward the distal tip 38 position. Proximally sliding of the rod decreases the bending of the bendable segment 13 and thereby moving the distal tip 38 in opposite direction. The rod 15 is a guiding member and its distal tip to be advanced into vocal cords opening and guides the ET 40 into the vocal cords opening and trachea.

From the proximal to distal end of the rod 15 includes a proximal segment 11, a middle segment 12, and a bendable segment 13, and a tip segment 32. Or it can be described as bendable portion of the rod 15 which is the bendable segment 13 and non-bendable portion of the rod which is the proximal and middle segment of the rod 15. A circle shaped ring, call control ring is attached to the most proximal end of the rod. From the proximal to distal direction, the bendable segment 13 can be further divided into first bending section 30, and second bending section 31. The junction of the first bending section 30 and second bending section 31 is configured to be bendable with 110-165 degree angle, called bending section joint 18. The tip segment 32 is connected with the distal end of the second bending section 31, called the tip segment junction 37. From the distal tip 38 of the tip segment 32 to the bending section joint 18 is defined as the distal portion of the bendable member, the rod. The tip segment junction 37 is a preferred attachment area for the retracting string distal end 36, also called the retracting string distal attachment 36, and is not designed to be bent. However the retracting string distal end 36 can couple along the distal portion of the rod. The junction of the bendable segment 13 and middle segment 12 of the rod is also bendable and is called bendable junction 17. The bending section joint 18 is easier to bend than the bendable junction 17 and is to be bent first.

Alternatively the bendable segment 13 can be just one segment with flexibility and elasticity therefore there is no the first bendable point. Further alternatively the bendable segment 13 can be configured in more than two bending sections up to twelve multiple small bending sections with multiple bending section joints in which each bending section and each bending section joint can contribute a smaller amount of the bend. Therefore cumulatively all small bends form a big curvature.

Different segments of the rod 15 are designed to have different cross section diameter and withstand different physical forces. The proximal segment 11 and middle segment 12 of rod have a bigger diameter which is strong enough not to be significantly bent and mostly keep its original shape when being pushed by an operator and is able to transmit the operator's pushing force distally to the bendable segment 13. The operator's pushing force is force required to overcome the friction of the stylet sliding through the tube to bend the bendable segment, and any force to overcome the friction and interactions between the distal tip 38 of the stylet and throat structures. The cross section of the rod 15 is changeable over its length and can be many geometric shapes, such as square, rectangle, trapezoid, triangle, round, semi-circle, ellipse, semi-ellipse, diamonds, rhombuses, pentagons, or combinations. In contrast, the first bending section 30 and second bending section 31 of the bendable segment 13 has smaller diameter in cross section and is thinner than the middle segment 12 and proximal segment 11. Alternatively the bendable segment 13 can be made of different materials with flexibility and elasticity. The bendable segment 13 is only portion of the rod 15 to bend significantly and can form curves and thereby move the tip segment to a target position. The first bending section 30 and second bending section 31 can be configured as preferably thinner elongated with semi-ellipse or semi-circle shaped in cross section. The flat side of semi-ellipse shaped in cross section will face up to the retracting string 19.

The tip segment 32 is crescent shaped with its distal tip 38 slightly facing down and connected with distal end of the second bending section 31 at the tip segment junction 37. The cross section of the tip segment 32 can be configured to be a round shape, elliptic shaped, or same shape as two bending sections. The bottom surface of the tip segment junction 37 is smooth round shaped. The upper surface of the tip segment junction 37 will be attached at the retracting string distal attachment 36. When the retracting string distal attachment 36 is approaching the tip segment junction 37, it spreads wider and attaches upper surface and bilateral sides of the tip segment junction 37 which will make the tip segment junction not easily bendable by a usually used force in an airway device.

Referring to FIG. 5, illustrating the distal structures of the device, the first bending section 30 and second bending section 31 are resiliently flexible and can bend when the rod 15 is being pushed distally and the retracting string 19 is pulling on the tip segment junction 37. The bending or curvature formation are formed by tension between the tip segment junction 37 and the ET distal aperture 43 produced by the stretched distal retracting segment 22 of the retracting string 19. The bending section joint 18 is configured to readily bend and plays a major role in curvature formation at early bending stage which is during the first and second push of the rod in present invention. The bendable junction 17 can be bent any significate amount only at later stage push which is third push in the present invention. The bendable junction17 only can be bent when it is near or already out of the ET distal aperture 43 which happens during third push in in which the third transverse protrusion 67 can be docked with the docking hole 55. The bendable junction 17 is configures to be stiff enough to withstand the first and second push without being significantly bent and can transmit the pushing force from the proximal and middle segment to the bendable segment 13. After second push, a majority length of the first bending section 30 is outside of the ET distal aperture 43 and the coiled filament 21 of the retracting string 19 is fully stretched, and now the retracting string 19 has reached its maximum length and is no longer be stretchable because the retracting string proximal attachment 56 is fixed to the docking plate and is not movable, therefore the retracting string will have a holding power to hold the bendable segment 13 backward and form a curve, or articulating the bendable segment 13.

In general each segment of the rod 15 has a larger cross section area and is stiffer and stronger than the retracting string 19, so a distal movement of the rod 15 will pull more the retracting string outside of the ET distal aperture 43 and tighten the retracting string 19. In other hand the extensibility of the retracting string allows the rod being pushed out the ET distal aperture, but in limited predetermined distance. Therefore the retracing string can generate or hold retracting force to the bendable segment of the rod. Consequently the retracting string will hold the bendable segment 13 of the rod 15 backward to bend or form a curve and move the distal tip 38 position when the rod is being pushed forward. These two opposite forces create the bending curvatures. The bendability of bendable segment the rod and the extensibility of the retracting string are essential for curvature formation outside of the ET distal aperture. During whole process of the bending, the distal retracting segment 22 of the retracting string 19 is contacting the upper part of the ET distal aperture 43, most likely the upper edge 49 of the ET distal aperture 43. The upper edge 49 of the distal aperture 49 will serve as a pivot point or anchor point for the retracting string 19, more precisely the distal retracting segment 22, to convey its tension to hold back the distal end of the bendable segment 13 and serve as sliding point for the distal restricting segment to swing back and forth when the rod is moving back and forth along the inside of the ET.

There are few factors or mechanisms involved in articulating the bendable segment 13. The position of the tip segment 32 and the curve formation of the bendable segment 13 are controlled by the extensibility and tension on the retracting string 19, the number of the bendable points, the position of the bending section joint 18, the bendable junction 17, the number of the bending section in the bendable segment 13, flexibility and length of the first and second bending section 30, 31 extensibility of the retracting string 19 and length of the bendable segment 13 inside of the ET lumen at the set-up position. The length of the both bending section 30, 31 can be variable and diameter of each section can be same or different. By manipulating those variables, the present invention can be modified in different embodiments and obtain an optimal result. And as above described, the beginning of set up position, the distal position of the device is outside of an ET. However alternatively, the whole stylet can put inside of the ET at the set-up position and slide out during the operation. In both scenarios the curvature formation processes is all executed outside of the ET's distal aperture 43. This is important feature of the present invention. All these variations are within the scope of the present invention.

Alternatively the retracting string 19 can be designed to be pulled by the an operator causing the retracting string 19 to pull the bendable segment 13 of the rod 15 and generate the curvature formation and the distal tip 38 movement. In a further alternative embodiment the retracting string 19 can be pulled by an operator in addition to the rod being pushing forward. As long as majority length of the rod and the retracting string is inside of the ET with these two opposite forces increasing, and the operator's finger or fingers control one or two of these forces, the bendable segment 13 of the rod 15 will be bent.

The distal tip 38 of the tip segment 32, also called distal tip of the rod 15 or distal tip of the device, has smooth and slippery surface. Preferably the tip segment 32 can have a bigger diameter in cross section than the second bending section 31 which will give the tip segment 32 more rigidity to withstand more resistance. The tip segment 32 can be manipulated by the operator as result of the changes in bending in bendable segment 13 and cannot be substantially flexed or deviated by the pulling force of the retracting string 19 and bending process. The distal tip 38 of the tip segment 32 may encounter the resistance from surrounding tissues when the tip segment is pushed towards vocal cords opening, and thereby the tip segment 32 may be bent in small amount. But the resilient property of the tip segment 32 will resume its original shape once the resistance is passed or overcome during an operator's pushing the rod 15. Once the distal tip 38 has entered the vocal cords opening, the operator' hand will feel "loss of resistance" because the vocal cords opening has no resistance. Therefore, even if the location of vocal cords can only be barely seen or can only be estimated, the operator can push the rod toward that direction, the tip segment 32 is able to be bent slightly to "negotiate" with surrounding tissue and "find" its way to vocal cords opening which has no resistance. The tip segment 32 is configured as crescent shaped tip in its long axis with its distal tip 38 pointed slightly down which is much easier to align the vocal cords opening than prior arts devices. And at the same time the distal tip 38 is configured with sufficient flexibility to be moved around the laryngeal inlet area without damaging any tissues. The surface of the tip segment 32 is very slippery either by well lubricating before its use or being made of low coefficient of friction materials, such as coating of polytetrafluoroethylene (PTFE) material or similar materials, or combination the both. Once the distal tip is slid into the vocal cords opening, the ET can be slid along the stylet and into the trachea.

The retracting string 19 is a continuous elongated flexible extensible string and can be configured as three different shaped segments with smaller cross section area than the rod 15. It is designed to hold back the bendable segment 13 when the bendable segment 13 is pushed forward distally. It can be divided and described as a proximal filament 20, a coiled filament 21 and a distal retracting segment 22 or described as an extensible segment or non-extensible segment. It has a distal end, called the distal retracting segment 22, which is attached to the tip segment junction 37, or alternatively to the distal portion of the rod. It has a proximal end, called proximal attachment 56 which become thicker and is firmly attached to the lower surface of the docking plate 50, or alternatively to the holding plates 61. Because the docking plate 50 will not move during the curvature formation of the bendable segment 13, using the proximal attachment 56 generates tension or a holding force on the retracting string 19 when the retracting string 19 is taut and pulling the tip segment junction 37. Therefore, the tension will be built retracting from its proximal attachment and to its distal attachment 36 during bending and curvature formation. The coiled filament 21 is located between the proximal filament 20 and distal belt 22. The coiled filament 21 is coil like shaped that can be pulled straight and longer and at same time can generate the pulling force by its elastic recoiling. The retracting string 19 is in its loose and natural relaxed state before being assembled in set-up positon. When the device is assembled into set-up position, the proximal filament 20 and distal retracting segment 22 are kept straight, but the coiled filament 21 is still coiled and is not yet stretched. The distal retracting segment 22 of the retracting string 19 is preferably configured as thin belt shaped. The flat belt surface will be put against the upper edge 49 of the ET distal aperture 43 by the operator at set-up position. The distal end of the distal retracting segment 22 is the retracting string distal attachment 36, preferably is spread wider can wrap around top and partially right and left side of the tip segment junction 37. Therefore, the retracting string distal attachment 36 can reinforce and keep the tip segment junction 47 from being easily twisted while the operator moving the distal tip 38 through manipulation of the rod 15.

And because the distal retracting segment 22 of the retracting string 19 is preferably configured in a belt shaped, during the operation the belt shaped distal retracting segment 22 will be kept facing and moving against the upper edge 49 of the ET distal aperture 43. Therefore, the distal retracting segment 22 of the retracting string 19 will be always positioned above the rod 15 and will not be easily twisted which will further help the tip segment in upright position. This positional relationship is also reinforced by the belt shaped intersegment 28.

The extensibility of the coiled filament 21 is essential for rod 15 moving distally out of the ET distal aperture 43 at early pushing stage. The coiled filament 21 is configured to be fully extended straight with no more extensibility rafter pushing the rod 15 to the second docking position or after second push. Alternatively it can be configured to have more extensibility even after third push. And alternatively the coiled filament 21 can be modified as a folded filament folding inside of the ET's lumen readily to be extended. Further alternatively, the coiled filament can be omitted, so the bendable segment of the rod cannot move further outside of the ET distal aperture but still can be bent to form curvatures. And further alternatively, the whole or most portion of the retracting string can be constructed as an extensible filament, or belt shaped coil.

The retracting string 19 is preferably made of plastic or polymers, or metal wire, or other materials with comparable properties.

Referring to FIGS. 6a and 6b, the control handle 60 includes a docking plate 50 and two or more holding plates 61. Preferably, there are only two holding plates 61, one on right side of the docking plate 50 and another on left. Alternatively, third holding plate can be constructed at front edge of the docking plate 50. Construction of the right and left holding plates 61 start on the right and left edge of the docking plate 50 and extend downward or distally. As the holding plates 61 extending distally they are tapered toward each other and the space between them become narrower therefore they can hold an ET in the middle tightly. And the holding plates 61 also provide a place for an operator's thumb and other fingers to hold the ET 40 except one finger to put into the control ring 14, after the device is inserted inside of the ET. On lower portion of the left of the holding plate 61, two ET barriers 65, 66 are configured, one on front edge of the left holding plate, called front ET barrier 66, and one on back edge of the left holding plate, called back ET barrier 65. The front and back ET barriers function as a barrier to prevent the ET from moving toward the front and back during the operation. The right and left of holding plates 68, are a wave shaped thin plate with two depressions 62, 63, a first holding depression 62 and a second holding depression 63. At set-up position, the first holding depression 62 and second holding depression 63 of the right and left holding plate will compress and tightly hold an ET and an operator's fingers will grab both holding plates 61 to further tightly hold the ET 40 to restrict movement of an ET 40 during operation.

The control handle's docking plate 50 is a flat plate and perpendicular to the axis of the ET and the rod 15 at the set-up position. The docking plate 50 is configured to have a sliding hole 58, two docking hole barriers 53, and a docking hole 55. The sliding hole 58 has an opening entrance for an operator to put the rod 15 inside of the sliding hole 58 and then put both the rod 15 and the retracting string 19 inside of the ET lumen. Now completely closed circle shaped ET proximal aperture will prevent the rod 15 from moving out of the sliding hole 58. Because the ET is also being hold tightly by two holding plates, the rod 15 can move only up or down along the sliding hole inside an ET lumen and can only be moved out of the sliding hole 58 by an operator. Between the sliding hole 58 and the docking hole 55, there are two triangular shaped docking hole barriers 53, one on left and another one on right. The space between the two docking hole barriers 53, like a narrow door, only allows the rod go through but not the transverse protrusions 67-70. The docking hole 55 is anteriorly located and only allows the rod 15 sliding proximally and distally but not the transverse protrusions 67-70. In contrast, the sliding hole 58 is configured with a bigger hole for the rod 15 and all transverse protrusions 67-70 passing through freely when the rod is being pushed or pulled by an operator. Therefore, once the rod has been driven into the docking hole 55 by an operator, the elasticity of the rod 15 will bounce and press proximally. Therefore, the upper surface of the transverse protrusions 67-70 will contact the lower surface of the docking plate 50 and all transverse protrusions are not able to pass through, therefore stop there, called docking position or engagement position.

The control handle 60 preferably is made materials with some plasticity but with more rigidity than the retracting string 19, intersegment 28 and the rod 15. They can be molded together during the manufacture.

Referring to FIG. 1, 4, 5, 7, 8, 9, a thin belt shaped short length segment, called intersegment 28, is positioned between the distal retracting segment 22 of the retracting string and the bending section joint 18. The intersegment 28 has two ends or attachments, one is a string attachment 27 which is attached to the distal retracting segment 22 of the retracting string 19 and another is a rod attachment 26 which is attached to the bending section joint 28 of the rod 15. Preferably the rod attachment 26 spreads wider along the bending section joint 18. At set-up position the intersegment 28 is relaxed serpentine belt shaped and is slanted between the string attachment 27 and the rod attachment 26. At the set-up position the string attachment 27 is more distally positioned than the rod attachment 26. From beginning of the push to the later stage push which is third push, the intersegment 28 is gradually stretched fully and its string attachment 27 will become more proximal than its rod attachment 26 which is reverse of their original position orientation.

Preferably the rod attachment 26 of intersegment segment 28 is becoming more belt shaped when approaching and attaching the distal retracting segment 22 of the retracting string 19. The two belt surface conformably fuses together which will helps to keep the belt shaped distal retracting segment 22 of the retracting string above the bendable segment 13 and to avoid being easily twisted.

One of the functions of the intersegment 28 is to hold the bendable segment 13 and distal portion of the distal retracting segment 22 of the retracting string 19 in proximity during the curvatures formation. Another function is being used as part of the pulling tool to pull the bendable segment 13 during the third push. During the third pushing, the intersegment is fully taut and the intersegment become a straight line or an almost straight line to be used to hold the bending section joint 18 backward and to bend the bendable junction 17.

Alternatively, more than one up to three intersegments can be configured and they can couple to the distal retracting segment 22 and the bendable segment 13. And in a further alternative embodiment, the intersegment can be omitted.

Referring FIGS. 1, and 7, there are four transverse protrusions 67-70 spread over a length of the proximal segment 11 of the rod. They can be spaced out evenly or not evenly. Transverse protrusions 67-70 can transversely branch out from right, left front or back side of the body of the rod and are perpendicular to the longitudinal axis of the rod 15. They can be shaped in a variety of geometric shapes, such as cubic, or rounded objects, preferable a cubic-like. Correspondently, they designate three pushes for three positions or three docking positions. The most proximally located transverse protrusion is for docking the device in the set-up position, call set-up transverse protrusion 70, then consequently first transverse protrusion 69 is for measuring first push distance and docking the rod at first docking position, second transverse protrusion 68 is for measuring second push distance and docking the rod at second docking position, and third transverse protrusion 67 is for measuring third push distance and docking the rod at third docking position. An operator can choose to push the rod 15 continuously or intermittently docking the rod. Alternatively, there can be more or less than four transverse protrusions. When an operator' finger push the control ring 14 and obtains a desirable the distal tip position under a vision of a laryngoscope or video laryngoscope, an operator's finger can drive the rod 15 into the docking hole 55 and dock the rod by putting nearest transverse protrusion into and under the docking hole 55, then the operator can focus attention on holding the control handle 60 and moving the distal tip 38 forward into the vocal cords opening. During this process if the operator finds that more movement of the tip 38 is needed, then the operator's finger can drive the rod out of the docking hole 55 into the sliding hole 58 and pushing forward or pulling backward the rod to increase or decrease the curvature of the bendable segment 13. The docking hole 55 does not allow the transverse protrusions 67-70 moving through, but it does allow the rod's 15 sliding movement, therefore operator still can push or pull the control ring 14 to move the rod distally or proximally between the two transverse protrusions which is a smaller distance.

Optionally pushing the rod distally by an operator can performed in a step by step fashion. Each push is pre-set distance by a transverse protrusion and the length and extensibility of the retracting string 19 is also pre-set too, therefore the each push can most likely produce a predictable curvature.

Each push and docking position is corresponding to a bending curvature of the bendable segment 13 and a position of the tip segment 32. It is predictable in large degree. But there can be some variability due to using different manufacture's ETs which can be different in wall thickness and even different components of manufacture materials.

Referring to FIG. 7a, at a set-up position, the set-up transverse protrusion 70 is docked into docking hole 55 below the lower surface of the docking plate 50. The ET 40 is held by the holding plates 61 below the lower surface of the docking plate. Loading an ET distal aperture 43 at the loading reference point 39 will leave distal portion of the device outside of the ET distal aperture 43 consistent, including a small portion of the first bending section 30, second bending section 31 and the tip segment 32, portion of the distal retracting segment 22 of the retracting string 19, and the intersegment 28 our side of the ET distal aperture 43.

Referring to FIG. 7b, the first push will slide more of the bendable segment 13 distally out of the ET distal aperture 43 which will pull retracting string 19 in same direction and stretch the coiled filament 21 about half of its stretching capability and reach the half of its final length. At same time, elastic recoiling force of the coiled segment 21 will pull the second bending section 31 back in proximal direction to cause the bending section joint 18 to bend, and thereby causing the tip segment 32 to be elevated. And the both bending sections 30, 31 can become more curve shaped and be pulled backward toward the ET anterior wall 47, therefore to form a curve along the bendable segment 13. This curvature or articulating formation is designed to accommodate the curve of the back of the patient's tongue. In a subsequent second and third push, an operator can adjust angle or configuration of the curve to move the distal tip 38 into the vocal cords opening. During all staged push process, the distal tip 38 of the tip segment 32 most likely will remain in its original slightly facing down position except when the distal tip 38 encounters an obstacle during this process. The intersegment 28 becomes more vertically positioned.

Referring to FIG. 7c, the second push will slide the bendable segment 13 further out of the ET distal aperture 43 which will further pull retracting string 19 distally. After the second push will double the length of the coiled filament 21 and will make the coiled filament become fully stretched and use up its all extensibility. In addition to the first push, the natural elastic recoiled capability of the coiled filament 21 is additively generating more pulling force to pull the second bending section 31 backward therefore to cause the bending section joint 18 bend more and the tip segment 32 elevation more. At same time the second bending section and first bending section may become more curvedly shaped. The intersegment 28 is becoming more vertically positioned and its two ends are reversing its proximal and distal orientation. The intersegment 28 is tightening. After second push, a majority length of the first bending section 30 is outside of the ET distal aperture 43 and the coiled filament 21 of the retracting string 19 has reached its maximum length, and because the retracting string proximal attachment 56 is fixed to the docking plate 50 or holding plates 61 which is not movable, therefore to create a holding force to hold the bendable segment 13 backward when the rod is advancing forward.

Referring to FIG. 7d for the third push, after second push the coiled filament 21 of the retracting string 19 becomes straight and has no more extensibility. During third push when the rod 15 is pushed and slid more distally, the retracting string 19 would more firmly hold the bendable segment 13 back toward the ET anterior wall 47. Therefore third push need the operator exert more pushing force and will push bendable junction17 outside of the ET distal aperture 43. Once the bendable junction17 is out of the ET distal aperture or just before outside of the ET distal aperture, the bendable junction will start to bend and the bendable segment 13 of the rod will form an angle with middle segment 12 of the rod. So the third push will generate a different shaped curvature which is largely produced by the bendable junction17 and elevate the position of the tip segment much more. And same time the bending section joint 18 may play no role or even reverse some of its bend by previously first and second push. However final goal is to move the distal tip 38 into the vocal cords opening.

During third push the intersegment 28 will become fully stretched and two attachments position orientation reversed, and then it will be used as a portion of pulling tool together with the distal retracting segment 22 to pull the whole bendable segment 13 backward therefore to bend the bendable junction 17. The retracting string distal attachment 36 will also pull the second bending section 31backward. These two pulling mechanisms work together to form a curvature and move up the distal tip 38 position.

Due to flexibility and elasticity of the materials of the device, even after third push the operator can still push the rod more distally in small amount to adjust the distal tip 38 positions if needed. And during the third push when the tension on the distal retracting segment 22 and whole retracting string 19 is high, the ET distal segment 45 can be lifted up a small amount. And the operator can rotate the control handle which will cause rotating the bendable segment 13 and the tip segment 32, therefore the operator can have more freedom to manipulate the distal tip.

Overall, the set-up transverse protrusion 70 corresponds to set-up position of the device. The first transverse protrusion 69 corresponds to the first push or first docking position. The second transverse protrusion 68 corresponds to the second push and second docking position. The third transverse protrusion 67 corresponds to the third push and third docking position.

The curvature generated by each push is cumulative. The third push will generate the largest bending curve and send the distal tip 38 farther and higher position if assuming a patient in spine position therefore to reach anteriorly located vocal cords opening which often is characteristic of a difficulty airway. An operator does not have to go all way to finish three pushes, once the distal tip 38 is near or in front of the vocal cords opening, the operator can stop pushing the control ring 14 and dock a corresponding transverse protrusion into the docking hole and focus on moving the distal tip into the vocal cords opening. However, the operator can choose to continuously push the control ring 14 without docking the rod at specific position until a desired distal tip 38 position results and then operator can advance the distal tip 38 of the rod into the vocal cords opening and trachea. Therefore, alternatively, the configuration of four transverse protrusions can be omitted, and above stated the staged push have been just served a purpose of easy describing and understanding.

Second Embodiment

FIG. 8, referring to second embodiment, at the distal end of the middle segment 12 of the rod 15 before continue with the bendable segment 22, a short segment of backward stem 80 has been configured which is continuation of the middle segment but turn posteriorly. The turning point 81 is anteriorly positioned against the anterior wall of an ET 40. The distal end of the backward stem 80 continues with the proximal end of the bendable segment 13 of the rod 15, also called bendable junction 17. The function of the bendable junction 17 is same as previously described embodiment. It will only be significantly bent during the third push, or after third push. The purpose of this design is alternative way to ensure at least most of the bendable segment 13 touch the ET posterior wall 46 during the first and second stage push, thereby does not move to anteriorly and possibly tangling with the retracting string 19. In a further alternative embodiment the intersegment 28 in the previously described embodiment can be omitted. The rest of elements, configurations and relationship toward each, working principle and functions in this embodiment are same.

In an alternative embodiments, the tubular structure can even be replace by other structures with similar shape, such as fenestrated tubular structure, or not similar a tubular structures but having same function as a tubular structure to hold the bendable member and retracting string in proximity, such as a coiled belt wrapping around the bendable member and the retracting string intermittently or continuously along the retracting string from proximal end to distal portion. And further, the present invention can embed a bundle of fiber-optic fiber into the bendable member along its long axis to make the device has its own "vision" which can make the device capable to be used independently without a laryngoscope. They are all within scope of protection of this invention.

Third Embodiment

Two modifications can be made to first embodiment to make the device to have capability to carry fiber-optic-scope probe to have its own "vision". FIG. 9a, 9b, 9c, referring to third embodiment, comprises the basic components same as first embodiment, a retracting string 19, a control handle 66 and an intersegment 28. All these three basic components have same configuration and functions. However the elongated bendable member 15 is modified as a flexible elongated shell shape to carry a fiber-optic scope probe, call bendable shell 85. This embodiment will also be assembled with an ET or tubular structure in the same way as the first embodiment.

In third embodiment, the bendable member 85 will also comprise a proximal segment, a middle segment, a bendable segment 75 and a tip segment 73 and has same length as the first embodiment. A control ring 14 is attached to the proximal end of the proximal segment. The bendable member has same two bendable points which is bending section joint 78 and bendable junction 77. The bendable segment 75 also partially extends outside the endotracheal tube distal aperture 43 at set-up position, and the bendable segment 75 also comprises a first bending section 71, a second bending section 72. The middle segment will not have the backward stem 80. The bendable segment 75 forms bendable junction 77 with middle segment same way as in the first embodiment and the second bending section 72 forms the bending section joint 78 with the first bending section 71 same way as the first embodiment. The bendable segment 75 can be flexed and form different curvatures configuration and change the distal tip position when the bendable member 85 is sliding distally in an ET 40 and when the retracting string 19 is pulling or holding the bendable segment 75 proximally, the same mechanism and configuration as in first embodiment.

The intersegment 28 is configured same and performed same function as in first embodiment. The control handle will be configured same and performed same function as in the first embodiment too. The rod' proximal segment will have same four transverse protrusions and set up three staged pushes.

Essentially there are only two different configurations in the third embodiment.

First is that the bendable member 15 comprises the same proximal segment, middle segment and bendable segment 75, but they are configured as a semi-open round elongated shell which can partially contain and carry a fiber-optic scope probe 83, called bendable shell 85. Preferably the opening side of the sell will be facing to posteriorly. As FIG. 9b1 illustrates in a cross section view, after the fiber-optic scope probe is pressed into the bendable shell 85, about half or more than half of anterior aspect of the circumference of the fiber-optic scope probe, in cross section, will be hold inside the shell, and posterior aspect of the fiber-optic scope probe 83 positioned outside the bendable shell 85 and will be facing or touching the ET posterior inner wall 46, after the device assembled together with the ET or during the operation. Since posterior aspect of the bendable shell 85 may contact the ET posterior wall, especially most portion of the posterior aspect of the first bending section 71 is configured to be against the ET posterior wall 46, therefore the fiber-optic scope probe 86 can be further pressed inside of the bendable shell 85 by the ET posterior wall 46. Further between the control ring 14 and the proximal side the third transverse protrusion 67, a fiber-optic scope probe proximal holder 87 has been configured. In cross section view, FIG. 9b2, the fiber-optic scope probe proximal holder 87 is a clamp located at the proximal segment the bendable shell that extends posteriorly to surround more circumference of the fiber-optic scope probe, therefore to further secure the fiber-optic-fiber probe inside of the bendable shell 85. But there is still an opening posteriorly which allow the fiber-optic scope probe to be taken out the bendable shell 85. For example, when an operator desires to further advance the fiber-optic scope probe after the fiber-optic scope probe is carried to a "hard to reached" narrow place by the device, the fiber-optic-scope probe can be separated from the bendable shell 85 and advance further.

Second difference is that about half-length of the tip segment 73 starting from middle of the tip segment to the end of distal tip 88, distal portion of the tip segment 73 is configured like a finger glove, called the fiber-optic-scope probe tip glove 89. The rest half length of the tip segment on the proximal side, the tip segment junction are configured the same as the semi-opened bendable shell 85 as described above. The fiber-optic-scope probe tip glove 89 has a down facing opening, called the fiber-optic-scope probe glove entrance 79, through which the fiber-optic-scope probe can be put into the fiber-optic-scope probe tip glove 89. The design purpose of the fiber-optic-scope probe tip glove 89 is to hold the fiber-optic-scope probe tip therefor the tip of the fiber-optic-scope probe could not easily come out while bending the bendable segment 13 and forming the curvatures. The distal tip 88 of the fiber-optic-scope probe glove 89 is transparent and can transmit light beyond the distal tip 88 of the device and images surround the distal tip area are transmitted back to the fiber-optic-scope display screen 86. The fiber-optic-scope can provides light for an operator to see anatomies surround the distal tip of the device directly if using the present invention under vision of a laryngoscope. Or the operator can use present invention independently and see the anatomies surround the distal tip of the device on the fiber-optic-scope display screen 86 without using a laryngoscope. Once the device has carried the fiber-optic scope probe to a desired destination, if the operator want to further advance the fiber-optic-scope probe to a farther destination, the operator can release the fiber-optic-scope probe from the fiber-optic-scope probe proximal holder 87 and pull back the fiber-optic-scope probe a little to let the tip of the fiber-optic-scope probe slide out the fiber-optic-scope probe tip glove 89. Once the tip of the fiber-optic-scope probe is out of the fiber-optic-scope probe tip glove 89, the operator can pull the device out of a patient's mouth and advance the fiber-optic scope probe without the use of the device.

What is claimed:

1. A stylet configured to be inserted inside of a tubular structure and to be pushed out a tubular structure distal aperture comprising:
    (a) an elongated bendable member having a longitudinal axis comprising a proximal segment, a middle segment, a bendable segment and a tip segment, wherein said bendable segment is in conjunction with the middle segment, wherein said conjunction between the bendable segment and the middle segment is configured to bend when a bending force is applied, and wherein the bendable segment of the bendable member is configured to be pushed beyond the tubular structure distal aperture, wherein the bendable segment has a distal end, wherein the distal end of the bendable segment is in conjunction with the tip segment, wherein the tip segment has a distal tip;
    (b) a retracting string running external along the entire length of the elongated bendable member, the retracting string comprising a non-resilient proximal end, a non-resilient distal end and a resilient portion, located between the non-resilient proximal end and the non-resilient distal end, wherein the distal end of the retracting string is attached to the distal end of the bendable segment of the bendable member, wherein the retracting string is configured to generate a retracting force when the retracting string is tauten therefore to hold the bendable segment of the bendable member backward when the bendable member is being pushed forward, and thereby forming curvatures along the bendable segment of the bendable member and moving the tip segment of the bendable member.

2. The stylet of claim 1, wherein the proximal segment and the middle segment of the bendable member are configured to transmit a pushing force exerted by an operator at a proximal end of the proximal segment to the bendable segment distally.

3. The stylet of claim 1, wherein the bendable segment is further configured to have two bending sections, wherein a first bending section and a second bending section of said two bending sections are flexible and resilient and can be bent when a bending force is applied.

4. The stylet of claim 3, wherein said first bending section is in conjunction with said second bending section, wherein said conjunction between said first bending section and said second bending section is configured to be bendable with a preformed angle of 110-150 degrees and is configured to bend when a bending force is applied.

5. The stylet of claim 3, wherein the bendable segment can be configured to have three or more bending sections in conjunction with each other thereby to form two or more than two bending points, wherein each bending point can be bent when a bending force is applied.

6. The stylet of claim 1, further comprising a control ring at the proximal end of the bendable member configured so that an operator can use a finger to push the bendable member distally and pull the bendable member proximally along the lumen of the tubular structure, thereby controlling the movement of the distal tip position of the device.

7. The stylet of claim 1, further comprising a control handle configured to couple said elongated bendable member and the retracting string together, wherein said control handle comprises a docking plate and two holding plates, wherein the docking plate provides a docking place for the bendable member to dock at a particular position, wherein the holding plates are configured to couple the tubular structure and the device together.

8. The stylet of claim 1, wherein the tip segment of the bendable member is configured to have a crescent shape in the longitudinal axis with the tip pointing down slightly to be easily aligned with a vocal cords opening.

9. The stylet of claim 8, wherein the tip segment is made of a flexible and resilient material and therefore able to bend when encountering an obstacle in a patient's soft tissue space.

10. The stylet of claim 1, wherein the resilient portion of the retracting string is a coiled filament, wherein the coiled filament is configured to be extensible in a predetermined and limited distance under a pulling force, wherein when the coiled filament is elongated, the coiled filament generates a pulling force to pull the bendable segment of the bendable member backward by a natural recoil elasticity of the coiled filament when the bendable segment of the bendable member is being pushed forward.

11. The stylet of claim 10, wherein the extensibility of the retracting string is configured to allow the bendable segment of the bendable member to be pushed out the tubular structure distal aperture.

12. The stylet of claim 1, wherein the retracting string is configured as belt-shaped, wherein the upper belt surface is configured to slide against the upper edge of the tubular structure distal aperture to keep the position of the non-resilient distal retracting end of the retracting string above the bendable segment.

13. The stylet of claim 12, wherein the non-resilient distal retracting end of the retracting string is configured to use the distal aperture as an anchor point to convey the tension of the retracting string to the distal portion of the bendable segment of the bendable member when the retracting string is taut.

14. The stylet of claim 13, wherein the retracting string has an extending length, and wherein the extensibility of the resilient portion of the retracting string is configured to enable the bendable segment of the elongated bendable member to move further distally.

15. A stylet configured to be inserted inside of a tubular structure and to be pushed out a tubular structure distal aperture comprising;
  (a) an elongated bendable member having a longitudinal axis comprising a proximal segment, a middle segment, a bendable segment and a tip segment, wherein said bendable segment is in conjunction with the middle segment, wherein said junction between the bendable segment and the middle segment is configured to bend when a bending force is applied, and wherein the bendable segment of the elongated bendable member is configured to be pushed beyond the tubular structure distal aperture and to be bent readily into different curvatures outside of the tubular structure distal aperture, wherein the bendable segment has a distal end, wherein the distal end of the bendable segment is in conjunction with the tip segment, wherein the tip segment has a distal tip;
  (b) an extensible retracting string located external to the elongated bendable member comprising a non-resilient proximal end, a non-resilient distal end and a resilient portion located between the non-resilient proximal end and the non-resilient distal end, wherein the distal end of the retracting string is attached to the distal end of the bendable segment of the bendable member, wherein the retracting string is configured to be extensible and to generate a retracting force when the retracting string is pulled therefore to hold the bendable segment of the bendable member backward when the bendable member is being pushed forward, and thereby forming curvatures along the bendable segment of the bendable member and moving the tip segment of the bendable member; and
  (d) a flexible intersegment coupled between the bendable segment of the bendable member and the non-resilient distal retracting end of the retracting string.

16. The stylet of claim 15, wherein the intersegment is positioned between the bendable segment of the bendable member and the non-resilient distal end of the retracting string, wherein the intersegment has a first attachment at a first end and a second attachment at a second end, wherein the first attachment attaches to the bendable segment of the bendable member and the second attachment attaches to the non-resilient distal end of the retracting string, and wherein said first attachment is configured to be shaped as a belt which will couple with a belt shape of the non-resilient distal retracting end of the retracting string.

17. The stylet of claim 16, wherein the intersegment is configured to be used as a part of a pulling tool to hold the bendable segment of the bendable member backward during a later phase of a push when the bendable member is pushed distally.

18. The stylet of claim 16, comprising more than one intersegment.

19. The stylet of claim 15, wherein the middle segment has a distal end, wherein the distal end of the middle segment is configured to have a backward stem segment at its distal end, wherein the backward stem is configured to turn posteriorly, the backward stem has a distal end in conjunction with the bendable segment, wherein the conjunction of the backward stem and the bendable segment is a bendable point.

20. A stylet configured to be inserted partially inside of a tubular structure and to be pushed out the tubular structure distal aperture comprising:
  (a) an elongated flexible bendable shell having a longitudinal axis comprising a proximal segment, a middle segment, a bendable segment, a distal portion and a tip segment, wherein said bendable segment is in conjunction with the middle segment, and wherein the bendable segment of the elongated flexible bendable shell is configured to be pushed beyond the tubular structure distal aperture and bend into different curvatures outside of the tubular structure distal aperture, wherein the bendable segment has a distal end, wherein the distal end of the bendable segment is in conjunction with the tip segment, wherein the tip segment has a distal tip, wherein the bendable segment is further configured to have a first bending section and a second bending section, wherein said two bending sections are flexible and resilient and bend when a bending force is applied, wherein said first bending section is in conjunction with said second bending section, wherein said conjunction between the first bending segment and the second bending segment is configured to be a bendable point with a preformed angle of 120-160 degrees and to bend when a bending force is applied, wherein said conjunction between the bendable segment and the middle segment is configured to be a bendable point and is configured to transmit a pushing force exerted by an operator to the bendable segment of the elongated flexible bendable shell and wherein the bendable segment is configured to only bend when it comes out the tubular structure's distal aperture;

(b) a retracting string external to the elongated bendable member comprising a non-extensible proximal portion at a proximal end, an extensible middle portion, an a non-extensible distal portion at a distal end, wherein the distal end of the retracting string is coupled to the distal portion of the elongated flexible bendable shell member, wherein the retracting string is configured to hold a retracting force when the retracting string is taut therefore to hold the bendable segment of the elongated flexible bendable shell backward when the elongated flexible bendable shell is being pushed forward, and thereby forming curvatures along the bendable segment of the elongated flexible bendable shell and moving the tip segment of the elongated flexible bendable shell.

21. The stylet of claim 20, wherein the bendable shell is shaped to reversibly hold a fiber-optic-scope probe, wherein the bendable shell further comprises a clamp configured to securely hold the fiber-optic-scope probe, wherein when the fiber-optic-scope probe is held inside the bendable shell, the bendable shell is configured to bend at said bendable points, and wherein the fiber-optic-scope probe can be separated from the bendable shell by an operator.

22. The stylet of claim 20, further comprising a fiber-optic-scope probe tip glove on the tip segment configured to reversibly hold the tip of the fiber-optic-scope probe, wherein the distal tip of the fiber-optic-scope probe tip glove is transparent.

\* \* \* \* \*